US008388990B2

(12) United States Patent
Morelli et al.

(10) Patent No.: US 8,388,990 B2
(45) Date of Patent: *Mar. 5, 2013

(54) ACIDIFIED CHLORITE COMPOSITIONS CONTAINING NITROGENOUS STABILIZERS AND SYSTEMS AND METHODS RELATED THERETO

(75) Inventors: Joseph Morelli, Bothell, WA (US); Kelly Walker, Seattle, WA (US); C Cayce Warf, Jr., Woodinville, WA (US)

(73) Assignee: Ecolab USA Inc., St. Paul, MN (US)

( * ) Notice: Subject to any disclaimer, the term of this patent is extended or adjusted under 35 U.S.C. 154(b) by 1677 days.

This patent is subject to a terminal disclaimer.

(21) Appl. No.: 10/680,703

(22) Filed: Oct. 7, 2003

(65) Prior Publication Data

US 2004/0166136 A1    Aug. 26, 2004

Related U.S. Application Data

(60) Provisional application No. 60/417,019, filed on Oct. 7, 2002.

(51) Int. Cl.
*A01N 25/00* (2006.01)
(52) U.S. Cl. .......................... 424/405; 501/131; 501/137
(58) Field of Classification Search .................. 424/407, 424/601, 718, 602, 603, 605, 606, 661, 666, 424/703, 713, 714; 514/553, 554, 569, 570, 514/555, 556, 557, 558, 559, 560, 562, 567, 514/568, 571, 572, 573, 574, 576, 578, 601, 514/608, 665; 510/160, 161, 382, 383, 419
See application file for complete search history.

(56) References Cited

U.S. PATENT DOCUMENTS

| | | | | |
|---|---|---|---|---|
| 4,084,747 A * | 4/1978 | Alliger | ............................ | 422/20 |
| 4,288,428 A * | 9/1981 | Foll et al. | ....................... | 514/718 |
| 5,380,518 A * | 1/1995 | Roozdar | ........................ | 423/477 |
| 5,407,656 A | 4/1995 | Roozdar | ........................ | 423/477 |
| RE36,064 E | 1/1999 | Davidson et al. | ............. | 424/665 |
| 5,914,120 A | 6/1999 | Wellinghoff et al. | .......... | 424/406 |
| 6,071,483 A * | 6/2000 | Pastore | ......................... | 422/255 |
| 6,379,685 B1 * | 4/2002 | Richter et al. | .................. | 424/405 |
| 6,436,444 B1 | 8/2002 | Richter et al. | ................. | 424/665 |
| 6,524,624 B1 * | 2/2003 | Morelli et al. | ................. | 424/665 |
| 6,699,510 B2 | 3/2004 | McSherry et al. | ............. | 424/665 |
| 6,916,493 B2 * | 7/2005 | Morelli et al. | ................. | 424/665 |

FOREIGN PATENT DOCUMENTS

| | | |
|---|---|---|
| JP | 58-018617 | 2/1983 |
| WO | WO 02/23993 A2 | 3/2002 |

OTHER PUBLICATIONS

Kolar and Lindgren. Acta Chemica Scandinavica B 36, 1982 pp. 599-605.*

* cited by examiner

*Primary Examiner* — David J Blanchard
*Assistant Examiner* — Devang Thakor
(74) *Attorney, Agent, or Firm* — Andrew D. Sorensen; Amy J. Hoffman

(57) ABSTRACT

A two-part disinfecting system, as well as disinfecting compositions and methods for making and using the same. The two-part disinfecting system contains a first part and a second part adapted to be mixed to yield an aqueous acidic disinfecting composition, wherein the first part comprises a chlorite and the second part comprises an acid, and wherein the first part, the second part, or both the first and second parts further comprise a nitrogenous stabilizer having a nitrogen group substituted with at least one hydrogen.

40 Claims, 3 Drawing Sheets

ACIDIFIED CHLORITE COMPOSITIONS CONTAINING NITROGENOUS STABILIZERS AND SYSTEMS AND METHODS RELATED THERETO

CROSS-REFERENCE TO RELATED APPLICATION

This application claims the benefit of U.S. Provisional Patent Application No. 60/417,019 filed Oct. 7, 2002, which application is incorporated herein by reference in its entirety.

BACKGROUND OF THE INVENTION

1. Field of the Invention

The present invention relates to acidified chlorite compositions containing a nitrogenous stabilizer, as well as to two-part systems for generation of such compositions and to methods related to their use.

2. Description of the Related Art

Many diseases arise from the growth and spread of microorganisms that can affect all aspects of life, from human health, to animal health, to food and water safety, to the safety of the environments we live in. Disinfectants have found wide spread application in all these areas. Hospitals perform rigorous programs to disinfect and sterilize their environments. Consumer homes are replete with disinfectant hand cleaners, sprays, hard surface cleaners, disinfectant wipes, and fruits and vegetable washes. Disinfectants are widely used on farms where the difference between healthy and sick animals can mean the difference between profitability and loss.

Mastitis is one of the most common and economically costly diseases confronting milk producers. Economic losses result from poorer milk quality, lower milk production, and potential culling of chronically infected animals. The use of disinfectant solutions both before and after milking has found great success in preventing mastitis, particularly disinfectants based on acidified chlorite as commercially available from Alcide Corporation (Redmond, Wash.).

Acidified chlorite (AC) disinfectants are commonly two-part products having a first or "base" part containing a chlorite (such as sodium chlorite) and a second or "activator" part containing an acid activator. The AC disinfectant is formed upon mixing the first and second parts, and typically only in amounts sufficient for a given milking period. Depending upon the desired characteristics and/or intended use of the AC disinfectant, either the first or second part, or both parts, may contain one or more optional ingredients such as skin conditioners, healing agents, surfactants, thickeners, film-forming agents, and/or preservatives. Also, depending upon the two-part system, the AC disinfecting composition may be formed by simply mixing the first and second parts, often in approximately equal volumes, or may involve some additional dilution step before or after mixing.

Color has proved to be an important attribute for teat disinfectants, allowing farmers to visually confirm that the disinfectant has been properly applied to the teat. This is particularly advantageous for confirming application to large herds when multiple farm workers are applying the disinfectant to many different animals. Unfortunately, colorants often lead to the rapid consumption of chlorite, leading to a shorter useful lifetime than the same compositions without colorants.

Accordingly, there remains a need in the art for improved AC disinfectants generally. More particularly, there is a need to minimize the rate of chlorite consumption and/or chlorine dioxide formation in AC disinfectants, thus maximizing their useful lifetime. In addition, there is a specific need to extend the useful lifetime of AC disinfectants that employ colorants. The present invention fulfills these needs and provides further related advantages.

BRIEF SUMMARY OF THE INVENTION

In one embodiment, the present invention provides a two-part disinfecting system comprising a first part and a second part adapted to be combined to yield an aqueous disinfecting composition. The first part comprises a chlorite and the second part comprises an acid. In addition, the first part, the second part, or both the first and second parts further comprise one or more nitrogenous stabilizers which, as discussed in more detail below, are compounds containing a nitrogen substituted with at least one hydrogen. The first part, the second part, or both the first and second parts may further and optionally comprise one or more colorants.

When combined, the first part and second part form a disinfecting composition having utility over a wide range of applications. The presence of the nitrogenous stabilizer(s) has surprisingly been found to minimize the rate of chlorite consumption, and thus reduce the rate of chlorine dioxide generation, thereby providing a disinfecting composition that is longer lasting (and with less noxious odors). Furthermore, in disinfecting composition having one or more colorants, the nitrogenous stabilizer(s) have been found to be particularly effective. Such compositions are useful as teat dips, as well as for other disinfecting applications where extended lifetime is desirable.

In a further embodiment, a method for making a disinfecting composition is disclosed by combining the first part and the second part of the two-part disinfecting system. Such combination may involve mixing liquid forms of the first part and second part, or may involve diluting or dissolving the first part and/or second part prior to mixing, at the time of mixing, and/or after mixing.

In yet another embodiment, a method for disinfecting a substrate is disclosed by contacting the substrate with an effective amount of a disinfecting composition of this invention. Such substrates include any surface, material, or fluid that would benefit from being disinfected, including the skin or tissue of a warm-blooded animal, in particular the teat of a dairy cow, goat or sheep, as well as hard surfaces generally and food surfaces such as meat and meat parts (including beef, poultry, pork, other generally recognized red meats, and fish), fruits and vegetables, and process waters, such as flume waters, cooling tower waters, equipment, and facility cleaning solutions.

These and other aspects of this invention will be evident upon reference to the following detailed description of the invention. To that end, certain patent documents and other references are cited herein, which are hereby incorporated by reference in their entirety.

DETAILED DESCRIPTION OF THE INVENTION

Figure 1:
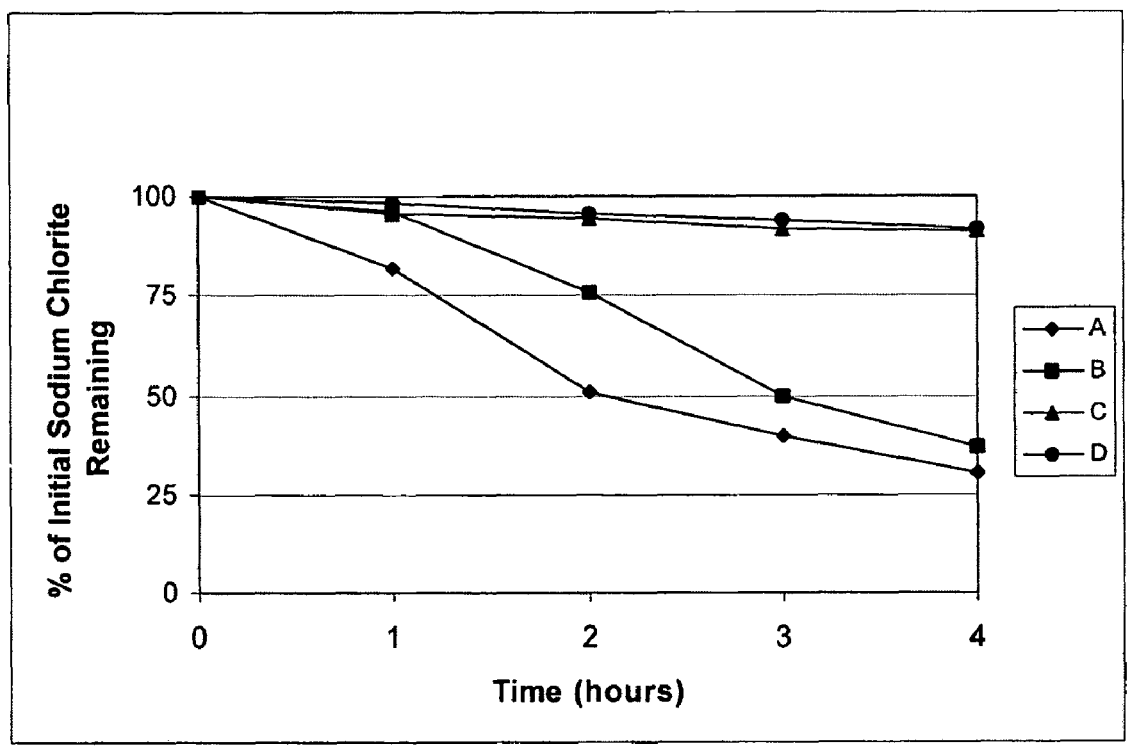
FIG. 1 illustrates the rate of sodium chlorite consumption for representative acidified chlorite compositions with a nitrogenous stabilizer, and without a nitrogenous stabilizer (control).

As noted above, in one embodiment a two-part disinfecting system is disclosed comprising a first part and a second part adapted to be combined to yield an aqueous disinfecting composition. The first part comprises a chlorite, the second part comprises an acid, and the first part, the second part, or both the first and second parts, further comprise a nitrogenous stabilizer. Optionally, the first part, the second part, or both the first and second parts further comprise one or more colorants.

Acidified chlorite compositions may be generated by combining chlorite (i.e., $ClO_2^-$), typically in the form of a metal salt such as sodium chlorite, with an acid activator. Such compositions are effective disinfectants due to the generation of antimicrobial oxidants, particularly chlorous acid (i.e., $HClO_2$). Chlorous acid is formed very rapidly upon acidification of chlorite in an equilibrium process governed by the solution pH. Chlorous acid can subsequently undergo a series of chemical reactions to form chlorine dioxide through various oxychlorine intermediates. Although not wishing to be limited by the following theory, it is believed that the nitrogenous stabilizer reduces generation of chlorine dioxide upon formation of the disinfecting composition by interacting with the oxychlorine intermediates in the conversion of chlorous acid to chlorine dioxide. When a colorant is present, it is degraded (e.g., oxidized) in significant part by the chlorine dioxide generated within the disinfectant. Thus, the nitrogenous stabilizer, by controlling chlorine dioxide generation, imparts extended color longevity to the disinfecting composition by limiting oxidation of the colorant. Chlorine dioxide is a particularly pungent gas that can be unpleasant and unhealthy at excessive levels in air. Unlike chlorous acid, which stays in solution at the surface being disinfected, chlorine dioxide can escape into the air around the user. Slowing the rate of chlorine dioxide formation leads to a longer lasting disinfectant composition with less noxious odors to the user.

The first and second parts of the two-part disinfecting system may both be in the form of an aqueous solution, emulsion, microemulsion, cream or gel, or one or both may be in a concentrated, non-aqueous or solid form. For example, the first and second parts may be aqueous solutions or gels to be mixed in approximately equal volumes to form the disinfecting composition, or may be concentrates or solids to be diluted by or dissolved in water, and then mixed to yield the disinfecting composition. Alternatively, the first and/or second parts may be in a non-aqueous or solid form (such as a powder or tablet) to be mixed with or dissolved in water prior to combination. To avoid excessive generation of chlorine dioxide, which may occur upon combination of concentrated forms, it is preferable to mix the first and second parts after the parts are diluted with or dissolved in water.

The chlorite of the first part is typically an alkali or alkaline earth metal chlorite, such as potassium or sodium chlorite, and more typically sodium chlorite. The chlorite is present in the first part in an amount such that, when combined with the second part, it is present within the disinfecting composition at a concentration ranging from about 0.005% to about 3% by weight, generally from 0.05% to 0.5% by weight, and typically from 0.1% to 0.4%.

The acid of the second part is any compound or mixture of compounds that will acidify the chlorite of the first part. In one embodiment, the acid has a pKa ranging from 2 to 5. The acid can be an organic acid, inorganic acid, or mixture thereof. Organic acids include (but are not limited to) formic acid, acetic acid, glycolic acid, lactic acid, pyruvic acid, malic acid, mandelic acid, citric acid, tartaric acid, adipic acid, succinic acid, malonic acid, propionic acid, heptanoic acid, octanoic acid, nonanoic acid, salicylic acid, benzoic acid, gluconic acid, or mixtures thereof. The organic acid can also be alkyl-, alkylarl-, and arylsulfonic acids such as octanesulfonic acid, toluenesulfonic acid, cumenesulfonic acid, dodecylbenzenesulfonic acid, and homo- & copolymers containing poly(styrenesulfonic acid) and poly(acrylamidopropylsulfonic acid). Inorganic acids include (but are not limited to) sulfuric acid, sodium bisulfate, phosphoric acid, hydrochloric acid, nitric acid, boric acid, or mixtures thereof. Other acids that may be used include (but are not limited to) hydrated metals salts of iron, aluminum, zirconium, vanadium, and gadolinium as described in U.S. Pat. No. 5,820,822. Acids also include (but are not limited to) solid acid exchange resins, such as Amberlite®, Diaion®, Dowex® and Duolite®, as well as aluminum silicate zeolites. Alternatively, the acid may be any organic acid precursor that forms an acid upon contact with water, such as acid anhydrides, esters, and sulfonate esters. Examples of organic acid precursors are described in U.S. Pat. No. 4,585,482.

In one particular embodiment, the acid of the second part is an organic acid such as glycolic, lactic, malic, mandelic, citric, tartaric, adipic acid, succinic acid, malonic acid, heptanoic acid, octanoic acid, nonanoic acid, benzoic acid, salicylic acid, gluconic acid, and mixtures thereof. In a further particular embodiment, the acid of the second part is an inorganic acid such as sulfuric acid, sodium bisulfate, phosphoric acid, hydrochloric acid, nitric acid, or a mixture thereof.

To the extent that some nitrogenous stabilizer of this invention can be classified as an acid, the acid of the second part is a different chemical entity than the nitrogenous stabilizer in those embodiments wherein the optional colorant is not present in the first part, the second part, or both the first and second parts. On the other hand, when the optional colorant is present in the first part, the second part, or both the first and second parts, both the acid of the second part and the nitrogenous stabilizer may be the same or different chemical entities.

The acid is present in the second part in an amount such that, when combined with the first part, it is present within the disinfecting composition at a concentration ranging from about 0.1% to about 10% by weight, generally from 0.5% to 5.0% by weight, and typically from 1.0% to 3.0% by weight. Alternatively, the amount of acid in the second part may be characterized by the pH of the disinfecting composition. In this regard, the acid is present in the second part in an amount such that, when combined with the first part, the pH of the disinfecting composition is below 5, generally from 1.5 to 5, and typically from 2.3 to 3.5.

The optional oxidizable colorant of the second part is a colorant that undergoes color loss upon contact with the acidified chlorite disinfectants. Such colorants are typically soluble in vehicles that may be used as carriers for the second part, including (but not limited to) water, alcohol, glycerin and/or oil. In the practice of this invention, either a single oxidizable colorant, or a mixture of two or more oxidizable colorants, may be present in the second part. The amount of oxidizable colorant present in the second part is an amount that, upon combination with the first part, will impart the desired color and/or color intensity to the disinfecting composition.

In the United States, colorants approved for use in foods, drugs, and cosmetics are regulated by the Food and Drug Administration (FDA) under 21 CFR parts 70 through 82. Colorants are generally classified as either (1) a food, drug and cosmetic (FD&C) colorant, (2) a drug and cosmetic (D&C) colorant, or (3) an externally applied drug and cosmetic (Ext. D&C) colorant, and the list of approved colorants are referenced therein. In Europe, colorants approved for use in foods and drug applications are outlined in European Parliament and Council Directive 94/36/EC 30 Jun. 1994 *Colours for Use in Foodstuffs*. Many colorants have more than one common name and may be identified using Colour Index Numbers (CI#) established by the Society of Dyers and Colourists (UK) and the American Association of Textile Chemists & Colorists (*Color Index*, Society of Dyers and Colorists and American Association of Textile Chemists & Colorists, Rev. 3$^{rd}$ ed, Branford, 1975). In addition, oxidizable colorants also include naturally occurring colorants such as red cabbage extract, beet root extract, carminic acid, curcumin, beta carotene, annatto extract, grape skin extract, astaxanthin, canthaxanthin, henna, guaiazulene, and mixtures thereof. Oxidizable colorants of this invention also include any combination of two or more of the above FD&C, D&C, Ext. D&C, and naturally occurring colorants. Furthermore, the oxidizable colorant may, upon contact with the first part, undergo a change in color. Such color change maybe attributable, for example, to a change in pH going from the pH of the second part to the pH of the resulting composition. Alternatively, the first part may optionally contain a colorant such that, when combined with the second part, the resulting composition has a color different from either first and second parts.

As noted above, it has been surprisingly found that the presence of a nitrogenous stabilizer in either the first part, the second part, or both the first and second parts, reduces the generation of chlorine dioxide and the consumption of chlorite in the resulting disinfecting composition. As a result, when an optional oxidizable colorant is present, the nitrogenous stabilizer imparts enhanced color and chlorite longevity to the disinfection composition. In this embodiment, the nitrogenous stabilizer and the acid of the second part can be the same chemical entity.

As used herein, a "nitrogenous stabilizer" is a nitrogen-containing compound having at least one N—H bond. Such a bond is present in both primary and secondary amines, but not tertiary amines. Such a bond is also present in certain carbamates, oxazolidinones, succinimides, and phthalimides. In this regard, representative nitrogenous stabilizers include (but are not limited to):

(1) $C_{1-12}$ primary and secondary alkylamines, such as butylamine, diethylamine, ethylhexylamine, decylamine, melamine, and imidazole;

(2) polyamines, such as ethylenediamine, diethyenetriamine, triethylenetetramine, tetraethylenepentamine, polyethyleneimines, polypropyleneimines, polylysine, polyvinylamine, and corresponding copolymers;

(3) primary and secondary substituted amines of $C_{1-18}$ alkylamidopropylamines; such as lauryl amidopropylamine;

(4) $C_{1-18}$ primary and secondary akanolamines, such as monoethanolamine, diethanolamine, tris(hydroxymethy) aminomethane, valinol, 2-amino-2-methyl-1,3-propanediol, 2-amino-2-ethyl-1,3-propanediol, 2-amino-1-butanol, 1-amino-2-propanol, 2-amino-1-propanol, 2-amino-2-methyl-1-propanol, and glucosamine;

(5) amino acids, such as glycine, alanine, valine, leucine, isoleucine, phenylalanine, tyrosine, tryptophan, serine, threonine, lysine, arginine, histidine, aspartate, glutamate, asparagines, glutamine, and sarcosine;

(6) arylamines, such as aniline, orthanilic acid, sulfanilamide, 2-amino-3-hydroxybenzoic acid methyl anthranilate, anthranilic acid, para-aminobenzoic acid, phenylenediamines, and aminophenols;

(7) primary and secondary aminosulfonates, such as, aminomethylsulfonate, aminoethylsulfonate (taurine), aminopropylsulfonate, and sulfanilic acid;

(8) primary and secondary amino derivatives of sulfamides, such as sulfamic acid, methylsulfamic acid, sulfamide, methylsulfonamide, phenylsulfonamide, toluenesulfonamide, aminobezenesulfamide, octane-2-sulfonic acid amide, and dodecylsulfonamide;

(9) N—H substituted carbamates, such as urea, methyl urea, butyl urea, biuretic acid, albiziin, allantoic acid, and ethyl hydantoate;

(10) N—H substituted cyclic carbamates, such as hydantoins, imidazolidinyl urea, glycolurils, and isocyanurates;

(11) N—H substituted oxazolidinones, such as 2-oxazolidinone and 4,4-bis(hydroxymethyl)-2-oxazolidinone; and

(12) N—H substituted succinimides and phthalimides, such as succinimide, 2,2-dimethylsuccinimide and phthalimide.

Alternatively, nitrogenous stabilizers of this invention may be represented by the following structure:

$$R_1\text{—NH—}R_2$$

wherein $R_1$ and $R_2$ are the same or different and, in the case of a primary amine, one of $R_1$ or $R_2$ is hydrogen, while in the case of a secondary amine neither $R_1$ nor $R_2$ are hydrogen. More specifically, $R_1$ and $R_2$ are the same or different and individually selected from hydrogen, alkyl, aryl, arylalkyl, heterocycle and heterocyclealkyl, each optionally substituted with one to six substituents.

Polymeric nitrogenous scavengers of this invention contain at least one monomeric repeating unit of the following structure:

$$\text{—[}R_1\text{—NH—}R_2\text{]—}$$

wherein $R_1$ and $R_2$ are the same or different and individually selected from alkyl, aryl, arylalkyl, heterocycle and heterocyclealkyl, each optionally substituted with one to six substituents. Polymeric nitrogenous scavengers may be linear or branched homopolymers or copolymers, and in the case of copolymers may be graft or block.

As used herein, the above terms have the following meanings:

"Alkyl" means a straight chain or branched, noncyclic or cyclic, unsaturated or saturated aliphatic hydrocarbon containing from 1 to 18 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Cyclic alkyls are also referred to herein as a "homocycles" or "homocyclic rings." Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

"Aryl" means an aromatic carbocyclic moiety such as phenyl or naphthyl.

"Arylalkyl" means an alkyl having at least one alkyl hydrogen atoms replaced with an aryl moiety, such as benzyl, —(CH$_2$)$_2$phenyl, —(CH$_2$)$_3$phenyl, —CH(phenyl)$_2$, and the like.

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

"Heteroarylalkyl" means an alkyl having at least one alkyl hydrogen atom replaced with a heteroaryl moiety, such as —CH$_2$pyridinyl, —CH$_2$pyrimidinyl, and the like.

"Heterocycle" (also referred to herein as a "heterocyclic ring") means a 4- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined above. Thus, in addition to the heteroaryls listed above, heterocycles also include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Heterocyclealkyl" means an alkyl having at least one alkyl hydrogen atom replaced with a heterocycle, such as —CH$_2$morpholinyl, and the like.

The optional substituent, as used in the context of R$_1$ and R$_2$ above, means any of the above groups (i.e., alkyl, aryl, arylalkyl, heterocycle and/or heterocyclealkyl) wherein at least one hydrogen atom is replaced with a substituent. In the case of an oxo substituent ("=O"), two hydrogen atoms are replaced. A "substituent" within the context of this invention includes halogen, hydroxy, cyano, nitro, amino, alkylamino, dialkylamino, alkyl, alkoxy, alkylthio, haloalkyl, aryl, arylalkyl, heteroaryl, heteroarylalkyl, heterocycle and heterocyclealkyl, as well as —NR$_a$R$_b$, —NR$_a$C(=O)R$_b$, —NR$_a$C(=O)NR$_a$NR$_b$, —NR$_a$C(=O)OR$_b$, —NR$_a$SO$_2$R$_b$, —C(=O)R$_a$, —C(=O)OR$_a$, —C(=O)NR$_a$R$_b$, —OC(=O)NR$_a$R$_b$, —OR$_a$, —SR$_a$, —SOR$_a$, —S(=O)$_2$R$_a$, —OS(=O)$_2$R$_a$ and —S(=O)$_2$OR$_a$, —OP(=O)(OR$_a$)(OR$_b$) wherein R$_a$ and R$_b$ are the same or different and independently hydrogen, alkyl, haloalkyl, aryl, arylalkyl, heterocycle, or heterocyclealkyl.

"Halogen" means fluoro, chloro, bromo and iodo.

"Haloalkyl" means an alkyl having at least one hydrogen atom replaced with halogen, such as trifluoromethyl and the like.

"Alkoxy" means an alkyl moiety attached through an oxygen bridge (i.e., —O-alkyl) such as methoxy, ethoxy, and the like.

"Alkylthio" means an alkyl moiety attached through a sulfur bridge (i.e., —S-alkyl) such as methylthio, ethylthio, and the like.

"Alkylsulfonyl" means an alkyl moiety attached through a sulfonyl bridge (i.e., —SO$_2$-alkyl) such as methylsulfonyl, ethylsulfonyl, and the like.

"Alkylamino" and "dialkylamino" mean one or two alkyl moiety attached through a nitrogen bridge (i.e., —N-alkyl) such as methylamino, ethylamino, dimethylamino, diethylamino, and the like.

In one embodiment, the nitrogeneous stabilizers have a "Reduced Chlorite Demand Factor" (RCDF) of 2 or greater, as calculated by the following equation (1):

$$RCDF = \frac{W_{test} \cdot V_{control}}{W_{control} \cdot V_{test}} \qquad \text{Equation (1)}$$

wherein W$_{test}$ is the weight (grams) of a test solution containing the nitrogenous stabilizer, W$_{control}$ is the weight of a control solution without the nitrogenous stabilizer, and V$_{test}$ and V$_{control}$ are the corresponding titration endpoints for the solutions. These various parameters may be determined for given potential nitrogenous stabilizer by the procedures set forth in Example 9.

Representative nitrogenous stabilizers of this invention include monoethanolamine, ethylenediamine, diethylenetriamine, triethylenetetraamine, polyethyleneimine, glycine, analine, serine, aspartate, glutamate, aniline, para-aminobenzoic acid, aniline sulfonic acid, methyl anthranilate, anthranilic acid, phenylenediamine, sulfamic acid, N-methysulfamic acid, aminomethylsulfonic acid, taurine, sulfonamide, sulfanilamide, benzenesulfonamide, toluenesulfonamide, urea.

In a more specific embodiment, nitrogenous stabilizers of this invention possess nitrogen groups that are substituted with two hydrogens (i.e., primary amines). Representative nitrogenous stabilizers include monoethanolamine, ethylenediamine, glycine, analine, serine, aspartate, glutamate, aniline, para-aminobenzoic acid, aniline sulfonic acid, methyl anthranilate, anthranilic acid, phenylenediamine, sulfamic acid, aminomethylsulfonic acid, taurine, sulfonamide, sulfanilamide, benzenesulfonamide, toluenesulfonamide, and urea.

The nitrogenous stabilizer is present in the first part, the second part, or both the first and second parts in an amount such that, when the first part and second part are combined, it is present within the disinfecting composition at a concentration ranging from about 0.001% to about 20% by weight, generally from 0.05% to 10% by weight, and typically from 0.1% to 5% by weight. Mixtures of nitrogenous stabilizers are also encompassed within this invention. For example, a first nitrogenous stabilizer may be present in the first part, and a second and different type present in the second part.

Various optional ingredients may also be present in the first part, the second part, or both first and second parts of the two-part system. Such ingredients include (but are not limited to) wetting agents, textural modifiers, film-forming polymers, surfactants, colorants and mixtures thereof. The wetting agents facilitate contact of the disinfecting composition with the skin or surface, and can be selected from those materials recognized to provide this effect, in both identity and amount. Textural modifiers are those materials which primarily affect the body of the mixed disinfecting composition in terms of retention, flow and lubricity. These include thickening agents such as alkyl celluloses, alkoxy celluloses, xanthan gum, guar gum, and polyacrylamide derivatives, of which the polymer of 2-acrylamido-2-methylpropane sulfonic acid is a preferred example. Inorganic thickening agents include hectorite, synthetic hectorite, magnesium aluminum silicate, bentonite, montmorillonite, and amorphous silicon dioxide. Thickening can also be achieved by a combination of anionic surfactants with amphoteric or zwitterionic surfactants and salt. Other textural modifiers include lanolin derivatives, acyl lactylates, polyethylene glycol, glyceryl esters, and mixtures thereof. Skin conditioning and skin healing agents include glycerin, sorbitol, pyrrolidone carboxylic acid, mineral oils, silicone oils, protein hydrolysates, petrolatum, hydrocarbon emollient alcohols and esters, allantoin, and urea. Film-forming polymers include the above-referenced polyacrylamides, as well as the class of poly(vinyl alcohols/vinyl acetates), polyurethanes, chitosan, polyvinyl pyrrolidone, and polyvinyl pyrrolidone copolymers.

For example, representative oral rinse and malodor compositions of this invention may contain the various ingredients as identified in Table 1.

TABLE 1

Representative Oral Rinse and Malodor Compositions

|  | Option 1 (Wt %) | Option 2 (Wt %) | Option 3 (Wt %) |
|---|---|---|---|
| Part 1 | | | |
| Sodium Chlorite | 0.32 | 0.08 | 0.32 |
| 1-Carvone | 0.10 | 0.10 | — |
| FD&C Green #3 | 0.09 | 0.09 | — |
| 1N NaOH | 0.10 | 0.10 | 0.10 |
| Sodium Fluoride | — | — | 0.10 |
| Water | q.s. | q.s. | q.s. |
| Part 2 | | | |
| Malic Acid | 0.75 | 0.27 | 0.75 |
| Sulfamic Acid | 0.25 | — | — |
| Glycine | — | 1.0 | — |
| Monosodium glutamate | — | — | 1.0 |
| L-Menthol | — | — | 0.03 |
| Sodium Benozate | 0.05 | 0.05 | 0.05 |
| Glycerin | 10.0 | 10.0 | — |
| FD&C Yellow #5 | 0.03 | 0.03 | — |
| FD&C Blue #1 | — | — | 0.0001 |
| Sodium Saccharin | — | — | 0.05 |
| Water | q.s. | q.s. | q.s. |

Similarly, a representative pre-operative skin antiseptic and a representative surface disinfectant are exemplified below:

| Part 1 | | Part 2 | |
|---|---|---|---|
| Representative Pre-Operative Skin Antiseptic: | | | |
| Sodium Chlorite | 4.00% | Mandelic Acid | 5.00% |
| Disodium Edetate | 0.19% | Methylsulfamic Acid | 0.10% |
| Isopropanol | 30.0% | Polyacrylamide | 0.75% |
| Polyethylene Glycol 4500 | 0.30% | Poloxamer 188 | 0.60% |
| Octylphenoxypolethoyethanol | 0.45% | Sodium Benzoate | 0.05% |
| Sodium Hydroxide | 0.075% | D&C Green # % | 0.01% |
| Water | q.s. | Water | q.s. |
| Representative Surface Disinfectant: | | | |
| Sodium Chlorite | 0.24% | Citric Acid | 2.00% |
| Tetrasodium EDTA | 0.23% | Sulfamic Acid | 1.00% |
| Sodium Hydroxide | 0.024% | Sodium Mono- & Dimethyl-Naphthalene sulfonate* | 0.36% |
| Water | q.s. | | 0.60% |
| | | Water | q.s. |

*Naxan ® ABL (Ruetgers-Nease)

Furthermore, a representative teat skin disinfectants are exemplified in Table 2 below:

TABLE 2

|  | Wt % | Wt % | Wt % | Wt % |
|---|---|---|---|---|
| Part 1 | | | | |
| Sodium Chlorite | 0.64 | 0.64 | 0.32 | 0.50 |
| Disodium Edetate | 0.20 | — | — | — |
| Tetrasodium EDTA | — | 0.20 | — | 0.045 |
| Cosmedia HSP 1180 | — | 15.00 | — | — |
| Sodium Hydroxide | 0.01 | 0.50 | 0.02 | 0.02 |
| Water | q.s. | q.s. | q.s. | q.s. |
| Part 2 | | | | |
| Lactic Acid | 2.5 | 1.5 | 5.2 | — |
| Mandelic Acid | — | 0.5 | — | — |
| Phosphoric Acid | — | — | — | 0.64 |
| Nonanoic Acid | — | — | 0.50 | — |
| Glycerin | 10.0 | 5.00 | — | — |
| Sorbitol | — | — | 1.00 | 3.00 |
| Sodium Dodecylbenzene Sulfonate | — | 0.50 | 0.75 | 0.25 |
| C14-16 Alpha Olefin Sulfonate | — | 0.50 | — | — |
| Decyl Glucoside | 0.25 | — | — | 0.25 |
| Sodium Benzoate | 0.05 | 0.20 | 0.04 | 0.04 |
| FD&C Yellow #5 | 0.30 | 0.30 | 0.30 | 0.04 |
| Hydroxyethylcellulose | — | 2.50 | — | — |
| Xanthan Gum | — | — | 0.30 | — |
| Polyvinyl alcohol/acetate | — | — | 2.00 | — |
| Urea | 3.5 | — | — | — |
| Toluenesulfonamide | — | 0.50 | — | — |
| Tetraethylenepentamine | — | — | 1.00 | — |
| Sulfanilamide | — | — | — | 0.25 |

In a further embodiment, a method for disinfecting a substrate is disclosed, wherein the method comprises contacting the substrate with an effective amount of the disinfecting composition formed by combining the first part and the second part of the two-part disinfecting system of this invention. In this context, the substrate may be any surface or material in need of, or that would benefit from, such disinfection, including (but not limited to) skin or tissue, as well as body fluids and mucosal membranes. For example, the substrate may be a wound where disinfection would aid healing. The substrate may be the inside of an animal's mouth where disinfection would help prevent gingivitis and halitosis. The substrate may include any item that is intimately placed in, on, or around the body of an animal, such as dentures, braces, and contact lenses. In a specific application, the substrate is the teat of a dairy cow, goat or sheep. In addition, the substrate may be any surface of a food product, such as meat, fish, fruits and vegetables. The substrate may also include food contact surfaces, and nonfood contact surfaces in food processing plants. The substrate may include any hard surface, such as (but not limited to) floors, walls, countertops, containers, instruments and/or equipment found in homes, hospitals, and manufacturing facilities. In a specific application, the hard surfaces may include housing and equipment surfaces in animal rearing and production environments. Materials that may benefit from disinfection include, for example, process waters, such as flume waters, cooling tower waters, livestock drinking waters, equipment and facility cleaning solutions.

In a further aspect of this invention, this invention is directed to a method for making a disinfecting composition comprising combining the first part and the second part of the two-part disinfecting system. In one embodiment, the first and second parts are both aqueous solutions, emulsions, microemulsions, creams or gels, and may be adapted to be combined in equal or different volumes. In another embodiment, at least one of the first or second parts is in a concentrated, non-aqueous or solid form, and the concentrated, non-aqueous or solid form is first diluted with or dissolved in water, and then combined with the other part. Alternatively, the dilution or dissolving step can occur prior to combination with the other part, or simultaneous with combination.

The following examples are provided for the purpose of illustration, not limitation.

Example 1

Representative Two-Part Disinfecting System and Resulting Disinfecting Composition This example illustrates the preparation of representative disinfecting compositions made by combining the first and second parts of two-part disinfecting systems. The disinfecting compositions include a typical disinfecting system and the corresponding simplified disinfecting system, with a nitrogenous stabilizer (Formulas C & D) and without a nitrogenous stabilizer (Formulas A & B) for comparison.

The first and second parts of the two-part system were as follows:

|  | Formulas (% w/w) | | | |
|---|---|---|---|---|
|  | A | B | C | D |
| Part 1 | | | | |
| Sodium Chlorite | 0.64 | 0.64 | 0.64 | 0.64 |
| Sodium Hydroxide | 0.022 | 0.022 | 0.022 | 0.022 |
| Na$_4$EDTA | 0.045 | 0.045 | 0.045 | 0.045 |
| Water | q.s. | q.s. | q.s. | q.s. |
| Part 2 | | | | |
| Lactic Acid | 2.64 | 2.64 | 2.64 | 2.64 |
| Sulfamic Acid | — | — | 0.50 | 0.50 |
| Triton X-100 | 0.153 | — | 0.153 | — |
| FD&C Yellow #5 | 0.30 | 0.30 | 0.30 | 0.30 |
| Glycerin | 10.00 | 10.00 | 10.00 | 10.00 |
| Hydroxyethylcellulose | 0.50 | — | 0.50 | — |
| Isopropanol | 2.00 | — | 2.00 | — |
| Sodium Benzoate | 0.04 | — | 0.04 | — |
| Sodium Hydroxide | — | — | 0.20 | 0.20 |
| Water | q.s. | q.s. | q.s. | q.s. |

(q.s. = quantum sufficit)

The two parts were then combined using equal volumes to yield a disinfecting composition having a pH of 2.5-2.7 and the following ingredients:

| Disinfecting | Formulas (% w/w) | | | |
|---|---|---|---|---|
| Compositions | A | B | C | D |
| Sodium Chlorite | 0.32 | 0.32 | 0.32 | 0.32 |
| Sodium Hydroxide | 0.011 | 0.011 | 0.111 | 0.111 |
| Na$_4$EDTA | 0.027 | — | 0.027 | — |
| Lactic Acid | 1.32 | 1.32 | 1.32 | 1.32 |
| Sulfamic Acid | — | — | 0.25 | 0.25 |
| Triton X-100 | 0.076 | — | 0.076 | — |
| FD&C Yellow #5 | 0.15 | 0.15 | 0.15 | 0.15 |
| Glycerin | 5.00 | 5.00 | 5.00 | 5.00 |
| Hydroxyethylcellulose | 0.25 | — | 0.25 | — |
| Isopropanol | 1.00 | — | 1.00 | — |
| Sodium Benzoate | 0.02 | — | 0.02 | — |
| Water | q.s. | q.s. | q.s. | q.s. |

The rate of sodium chlorite consumption over time was measured for each disinfecting system by potentiometric titration using potassium iodide and sodium thiosulfate with a Schott Titroline autotitrator and Schott 31RX platinum electrode. Samples were placed in 250 mL beakers and stirred vigorously for 1 minute to off gas any potential chlorine dioxide prior to determining the sodium chlorite levels. The results of these experiments are set forth in FIG. 1, with time zero being the time just after combining part 1 and part 2. Color intensity was also monitored using a Perkin Elmer Lambda 12 UV/Vis Spectrometer by making a 100-fold dilution by volume of the disinfecting system with deionized water and quantifying the absorbance at 425 nm with a 1 cm path length cuvette cell. The results of the color study are set forth in FIG. 2.

Figure 2:
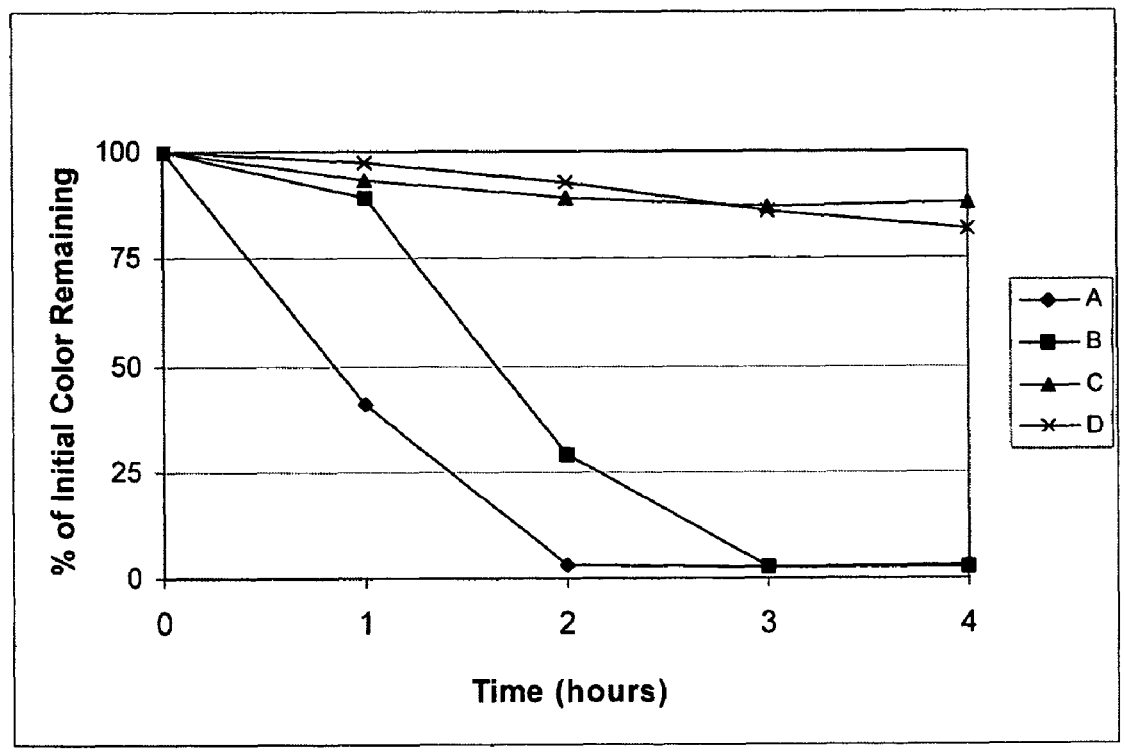
FIG. 2 illustrates the rate of color loss for representative acidified chlorite compositions with a nitrogenous stabilizer, and without a nitrogenous stabilizer (control).

FIGS. 1 and 2 show that sodium chlorite and color longevity can be substantially improved for disinfecting systems containing a nitrogenous stabilizer. Over the course of 4 hours, more than 60% of the sodium chlorite is consumed for Formulas A and B whereas less than 10% for Formulas C & D. In 4 hours, all the color intensity in Formulas A & B is lost, whereas Formulas C & D show less than 20% loss.

Example 2

Colorant Effect on Chlorite Consumptions

To determine how increasing levels of colorant causes a more rapid consumption of chlorite, the disinfecting composition A of Example 1 was prepared with either 0% (control), 0.03%, 0.15%, 0.30% or 0.60% by weight FD&C Yellow #5. The rate of sodium chlorite consumption over time was determined as in Example 1. The results of these experiments are set forth in FIG. 3.

This experiment was then repeated using essentially equimolar concentrations of the following FD&C colorants: 0.41% Blue #1, 0.26% Blue #2, 0.30% Yellow #5, 0.25% Yellow #6, 0.28% Red #40 and no colorant (control). The results of these experiments are shown in Table 3.

TABLE 3

| Colorant | Percent of Initial NaClO$_2$ Remaining 5 Hours after Mixing |
|---|---|
| FD&C Blue #1 | <2% |
| FD&C Blue #2 | 43% |
| FD&C Yellow #5 | 27% |
| FD&C Yellow #6 | 18% |
| FD&C Red #40 | 60% |
| No Color Control | 75% |

The results presented in Table 5 illustrate that various N—H containing compounds are effective in extending chlorite longevity. Methylsulfamic acid is a secondary amine and proved to be particularly effective. Aminomethanesulfonic acid and taurine are similar to sulfamic acid, but with the amino group separated from the sulfonic acid group by a methylene and ethylene spacer, and provided solid chlorite longevity benefits. The aniline, sulfanilamide, and aniline sulfonic acid examples demonstrate that compounds containing an aromatic amine group and/or a sulfonamide group can also promote greater chlorite longevity. Finally, urea demonstrates that an N—H group present in a carbamate also provides longevity benefits. From these and other examples it can be seen that an important structural feature is the presence of an N—H group, whether it is present in an amine, aromatic amine, sulfonamide, or carbamate functional group.

Figure 3:
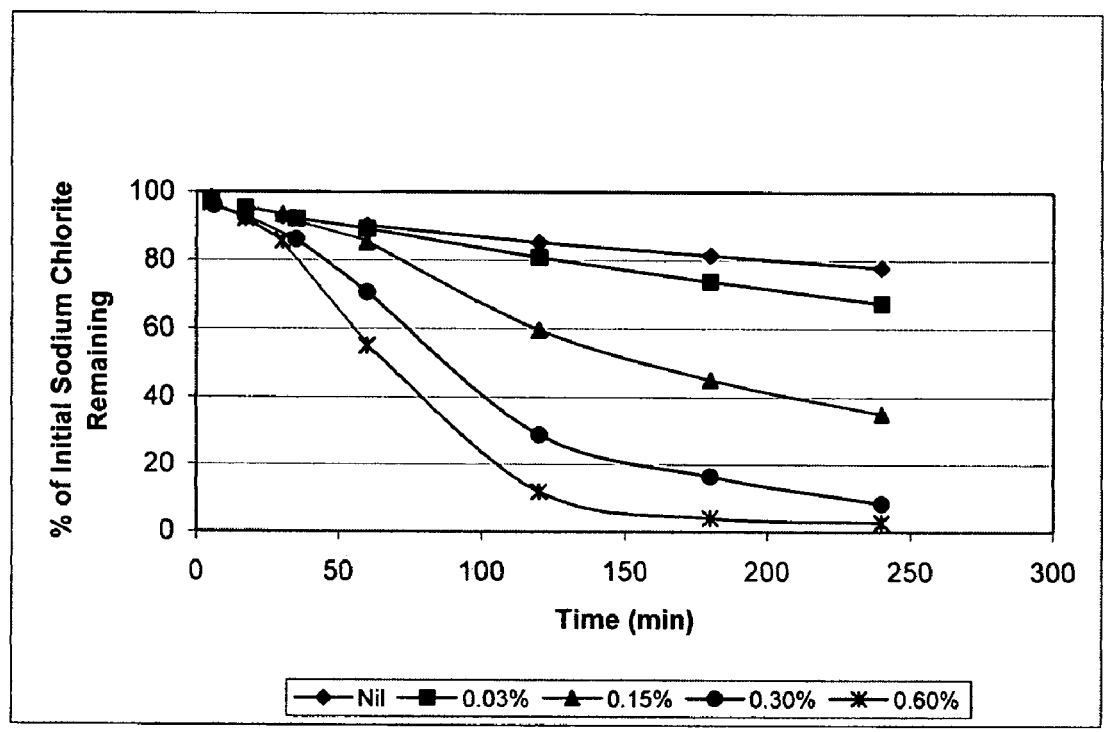
FIG. 3 illustrates the effect of FD&C Yellow #5 colorant levels on the rate of sodium chlorite consumption in a representative acidified chlorite composition.

As illustrated in FIG. 3 and Table 3, colorants cause an increased rate of chlorite consumption and the chlorite demand is proportional to the level.

Example 3

Effect of Nitrogenous Stabilizer on Chlorite Consumption

Equal volumes of one part aqueous sodium chlorite (0.64%) and a second part containing lactic acid (2.64%), FD&C Yellow #5 (0.30%), glycerin (10.0%), and the nitrogen-containing compounds listed in Table 4 were combined and the level of sodium chlorite was determined over time as in Example 1. The pH of the second part was adjusted for all compositions to achieve a mixed product pH of 2.5 using either aqueous sodium hydroxide or sulfuric acid. Other than sulfamic acid, the various nitrogen-containing compounds were compared at equal molar levels of nitrogen groups. The results of these experiments are presented in Table 4.

TABLE 4

| Nitrogen-Containing Compound | Level (Wt %) | Percent of Initial $NaClO_2$ Remaining | |
|---|---|---|---|
| | | 2 Hours after Mixing | 5 Hours after Mixing |
| Sulfamic Acid | 2.0 | 98% | 95% |
| Ethylenediamine | 2.0 | 92% | 80% |
| Monoethanolamine | 4.1 | 86% | 45% |
| Glycine | 5.0 | 78% | 42% |
| Triethanolamine | 9.9 | 5% | 3% |
| Nil Control | — | 63% | 11% |

As shown in Table 4, nitrogenous stabilizers of this invention having an N—H bond slowed the rate of sodium chlorite consumption, while a tertiary amine (i.e., triethanolamine), which does not contain an N—H bond, was found to accelerate the rate of sodium chlorite consumption.

Example 4

Effect of Nitrogenous Stabilizer on Chlorite Consumption

The experiment of Example 3 was repeated using nitrogenous stabilizers containing N—H bonds as listed in Table 5. Weight percentages were chosen to provide a relative comparison at equal molar levels of N—H groups.

TABLE 5

| Nitrogenous Stabilizers | Level (Wt %) | Percent of Initial $NaClO_2$ After 2 Hours | Percent of Initial $NaClO_2$ After 5 hours |
|---|---|---|---|
| Methylsulfamic Acid | 1.14 | 98% | 94% |
| Aminomethanesulfonic Acid | 1.14 | 86% | 57% |
| Taurine | 1.29 | 89% | 49% |
| Sulfonamide | 0.49 | 94% | 87% |
| Aniline | 0.96 | 95% | 87% |
| Sulfanilamide | 0.89 | 94% | 87% |
| Aniline Sulfonic Acid | 1.78 | 90% | 75% |
| Urea | 0.31 | 94% | 66% |
| Control | — | 66% | 13% |

Example 5

Effect of Nitrogenous Stabilizers on Color Consumption

Equal volumes of one part aqueous sodium chlorite (0.64%) and a second part containing lactic acid (2.64%), FD&C Yellow #5 (0.30%), glycerin (10.0%), and the nitrogen-containing compound listed in Table 6 were combined and the color intensity was measured by UV/Visible spectrophotometry at 425 nm over time to monitor color longevity. The pH of the second part was adjusted for all compositions to achieve a mixed product pH of 2.5 using either aqueous sodium hydroxide or sulfuric acid.

TABLE 6

| Nitrogen-Containing Compounds | Level (Wt %) | Percent of Initial Colorant Remaining 2 Hours after Mixing |
|---|---|---|
| Sulfamic Acid | 2.0 | 97% |
| Ethylenediamine | 2.0 | 91% |
| Monoethanolamine | 4.1 | 49% |
| Glycine | 5.0 | 61% |
| Triethanolamine | 9.9 | 1% |
| Nil Control | — | 3% |

The results in Table 6 show that those compositions containing nitrogenous stabilizers having an N—H bond have greater color longevity over the same compositions lacking the same. For example, triethanolamine, which is a tertiary substituted amine without an N—H group, did not provide color longevity benefits. (The weight percentages chosen for ethylenediamine, monoethanolamine, glycine, and triethanolamine were to provide a comparative molar level of nitrogen.)

Example 6

Effect of Nitrogenous Stabilizer on Chlorine Dioxide Generation

Equal volumes of one part aqueous sodium chlorite (0.64%) and a second part containing lactic acid (2.64%), glycerin (10.0%), and nitrogenous stabilizers listed in Table 7 were combined and the rate of chlorine dioxide generation was measured by UV/Visible spectrophotometry at 360 nm over time. The pH of the second part was adjusted for all compositions to achieve a mixed product pH of 2.5 using either aqueous sodium hydroxide or sulfuric acid.

TABLE 7

| Nitrogenous Stabilizer | Level (Wt %) | Level of $ClO_2$ after 1 hour (ppm) |
|---|---|---|
| Sulfamic Acid | 0.25 | 17 |
| Sulfamic Acid | 0.50 | 17 |
| Ethylenediamine | 1.0 | 35 |
| Monoethanolamine | 2.0 | 66 |
| Glycine | 2.5 | 105 |
| Nil Control | — | 128 |

The results in Table 7 show that formulations containing a nitrogenous stabilizer having an N—H bond slowed the rate of chlorine dioxide generation compared to the same formula without a nitrogenous stabilizer (i.e., nil control).

Example 7

Effect of Nitrogenous Stabilizers on Chlorite Consumption in a Nil Colorant Composition Equal volumes of one part aqueous sodium chlorite (0.64%) and a second part containing lactic acid (2.64%), glycerin (10.0%), and sulfamic acid (see Table 8) were combined, and the rate of sodium chlorite consumption was measured over time, as in Example 1.

TABLE 8

| Nitrogenous Stabilizer | Level (Wt %) | Percent of Initial NaClO$_2$ After 2 Hours | Percent of Initial NaClO$_2$ After 5 hours |
|---|---|---|---|
| Sulfamic Acid | 0.25 | 97% | 94% |
| Sulfamic Acid | 0.50 | 97% | 94% |
| Nil Control | — | 86% | 75% |

The results in Table 8 show that formulations containing a nitrogenous stabilizer slowed the rate of sodium chlorite consumption compared to the same formula without a nitrogenous stabilizer (i.e., nil control).

Example 8

Effect of Nitrogenous Stabilizer on Chlorite Consumption

Equal volumes of one part aqueous sodium chlorite (0.64%) and a second part containing lactic acid (2.64%), FD&C Yellow #5 (0.30%), glycerin (10.0%), and various levels of sulfamic acid (see Table 9) were combined and the rate of sodium chlorite consumption was measured over time, as in Example 1. The pH of the second part was adjusted for all compositions to achieve a mixed product pH of 2.5 using either aqueous sodium hydroxide or sulfuric acid.

TABLE 9

| Sulfamic Acid Level (Wt %) | Percent of Initial NaClO$_2$ Remaining after 2 Hours | Percent of Initial NaClO$_2$ Remaining after 4 hours |
|---|---|---|
| 0.0025 | 87% | 30% |
| 0.025 | 94% | 86% |
| 0.25 | 97% | 94% |
| 0.5 | 97% | 96% |
| 1.0 | 98% | 96% |
| Nil Control | 58% | 15% |

The results set forth in Table 9 show that sulfamic acid can significantly impact the rate of sodium chlorite consumption, even at levels as low as 0.0025%.

Example 9

Assay for Measuring the Reduced Chlorite Demand Factor

Representative nitrogenous stabilizers at 1.33 M concentration (or less if solubility limited) and polymeric derivatives are based on the molar concentration of the nitrogen monomeric repeating unit) were combined with lactic acid (2.64 wt %), FD&C Yellow #5 (0.30 wt %), and sulfuric acid or sodium hydroxide as needed such that the final mixed product with sodium chlorite had a pH of 2.5. Fifty grams of this solution was mixed with 50 grams of a 0.64 wt % sodium chlorite solution in a capped polyethylene container. A corresponding control sample without the nitrogenous stabilizer was prepared at the same time. Five hours after mixing, the sodium chlorite level was determined by potentiometric titration with potassium iodide and sodium thiosulfate. Approximately 10 gram samples of both the test and control solutions ($W_{test/control}$) were accurately weighed in 250 mL beakers with stir bars and the samples are vigorously stirred for 1 minute in a ventilation hood to off-gas any chlorine dioxide. Potassium iodide (2 g) was added followed by 10 mL of 0.5 N hydrochloric acid. The solutions were then diluted to a total volume of 175 mL with deionized water, and titrated with 0.1N sodium thiosulfate using a Schott Titroline (Schott Glas, Mainz, Germany) autotitrator and Schott Blueline 31RX (Schott Glas) platinum electrode. The titration endpoint was determined from the maximum of the first derivative of the titration curve for both the test and control solutions ($V_{test/control}$). The above values for each nitrogenous stabilizer tested were then inserted into equation (1) above to determine the Reduced Chlorite Demand Factor (RCDF). The results of this experiment are presented in Table 10.

TABLE 10

| Potential Nitrogenous Stabilizers | Reduced Chlorite Demand Factor |
|---|---|
| Sulfamic Acid | 4.5 |
| Ethylenediamine | 4.0 |
| Sulfanilamide* | 5.6 |
| Urea | 4.3 |
| Glycine | 3.8 |
| Monoethanolamine | 4.1 |
| Diethanolamine | 0.9 |
| Triethanolamine | 0.3 |

*Tested at 0.5% due to lower solubility.

As noted previously, in one embodiment of this invention, nitrogenous stabilizers have an RCFF of 2 or greater. In a more specific embodiment, the RCDF is 3.0 or greater, or in an even more specific embodiment is 4.0 or greater.

From the foregoing it will be appreciated that, although specific embodiments of the invention have been described herein for purposes of illustration, various modifications may be made without deviating from the spirit and scope of the invention. Accordingly, the invention is not limited except as by the appended claims.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

The invention claimed is:

1. A two-part disinfecting system comprising a first part and a second part adapted to be mixed to yield an aqueous acidic disinfecting composition, wherein the first part comprises an alkaline solution comprising an alkaline aqueous chlorite and a salt of sulfamic acid and the second part comprises an acidic solution comprising an aqueous acid and an oxidizable colorant, wherein the oxidizable colorant consists of a drug and cosmetic colorant, an externally applied drug and cosmetic colorant, a food, drug, and cosmetic colorant or mixtures thereof, and wherein the system is free of nonoxidizable colorants, and further wherein the system minimizes the production of chlorine dioxide formation as compared to if the salt of sulfamic acid were absent.

2. The system of claim 1 wherein the salt of sulfamic acid has a Reduced Chlorite Demand Factor of 2 or greater.

3. The system of claim 1 wherein the salt of sulfamic acid has a Reduced Chlorite Demand Factor of 3 or greater.

4. The system of claim 1 wherein the salt of sulfamic acid has a Reduced Chlorite Demand Factor of 4 or greater.

5. The system of claim 1 wherein the salt of sulfamic acid is present within the disinfecting composition at a concentration ranging from about 0.001% to about 20% by weight.

6. The system of claim 1 wherein the salt of sulfamic acid is present at a concentration ranging from about 0.05% to about 10% by weight.

7. The system of claim 1 wherein the salt of sulfamic acid is present within the disinfecting composition at a concentration ranging from about 0.1% to about 5% by weight.

8. The system of claim 1 wherein the chlorite is a metal chlorite.

9. The system of claim 8 wherein the metal chlorite is an alkali or alkaline earth metal chlorite.

10. The system of claim 8 wherein the metal chlorite is sodium chlorite or potassium chlorite.

11. The system of claim 8 wherein the metal chlorite is sodium chlorite.

12. The system of claim 1 wherein the chlorite is present in the first part in an amount such that, when combined with the second part, it is present within the disinfecting composition at a concentration ranging from about 0.005% to about 3% by weight.

13. The system of claim 1 wherein the chlorite is present in the first part in an amount such that, when combined with the second part, it is present within the disinfecting composition at a concentration ranging from 0.05% to 0.5% by weight.

14. The system of claim 1 wherein the chlorite is present in the first part in an amount such that, when combined with the second part, it is present within the disinfecting composition at an concentration ranging from 0.1% to 0.4% by weight.

15. The system of claim 1 wherein the aqueous acid is an organic acid.

16. The system of claim 1 wherein the aqueous acid is an inorganic acid.

17. The system of claim 1 wherein the aqueous acid is present in an amount such that, when combined with the first part, it is present within the disinfecting composition at a concentration ranging from about 0.1% to about 10% by weight.

18. The system of claim 17 wherein the inorganic acid is sulfuric acid, sodium bisulfate, phosphoric acid, hydrochloric acid, nitric acid, or a mixture thereof.

19. The system of claim 1 wherein the acid is a mixture of an organic acid and an inorganic acid.

20. The system of claim 1 wherein the acid is present in an amount such that, when combined with the first part, it is present within the disinfecting composition at a concentration ranging from about 0.1% to about 10% by weight.

21. The system of claim 1 wherein the aqueous acid is present in an amount such that, when combined with the first part, it is present within the disinfecting composition at a concentration ranging from 0.5% to 5.0% by weight.

22. The system of claim 1 wherein the aqueous acid is present in an amount such that, when combined with the first part, it is present within the disinfecting composition at an concentration ranging from 1.0% to 3.0% by weight.

23. The system of claim 1 wherein the aqueous acid is present in an amount such that, when combined with the first part, the pH of the disinfecting composition is below 5.

24. The system of claim 1 wherein the aqueous acid is present in an amount such that, when combined with the first part, the pH of the disinfecting composition ranges from 1.5 to 5.

25. The system of claim 1 wherein the aqueous acid is present in an amount such that, when combined with the first part, the pH of the disinfecting composition ranges from 2.3 to 3.5.

26. The system of claim 1 wherein the first part and the second part are adapted to be combined in equal volumes.

27. The system of claim 1 wherein the first part, the second part, or both the first and second parts further comprise a textural modifier, wetting agent, thickening agent, skin conditioner, healing agent, film-forming polymer, surfactant, preservative, or a mixture thereof.

28. A disinfecting composition formed by combining the first part and the second part of the two-part disinfecting system of claim 1.

29. A method for making a disinfecting composition comprising combining the first part and the second part of the two-part disinfecting system of claim 1.

30. The method of claim 29 wherein both the first part and the second part are in the form of an aqueous solution, emulsion, microemulsion, cream or gel.

31. The method of claim 29 wherein at least one of the first part or second part is in a non-aqueous or solid form, or is adapted to be diluted by or dissolved in water prior to combination of the first part and the second part.

32. The method of claim 31 wherein the non-aqueous or solid form is first diluted with or dissolved in water prior to contact with the other part.

33. A method for disinfecting a substrate comprising contacting the substrate with an effective amount of a disinfecting composition formed by mixing the two-part disinfecting system of claim 1.

34. The method of claim 33 wherein the substrate is skin or tissue of a warm-blooded animal.

35. The method of claim 33 wherein the substrate is a teat of a dairy cow, goat or sheep.

36. The method of claim 33 wherein the substrate is a hard surface.

37. The method of claim 33 wherein the substrate is a food surface or a surface in contact with food.

38. The method of claim 33 wherein the substrate is processing water.

39. The method of claim 33 wherein the substrate is cooling tower water.

40. The system of claim 1 wherein the salt of sulfamic acid is comprised of sulfamic acid or methylsulfamic acid or combinations thereof.

* * * * *